(12) United States Patent
Haddon et al.

(10) Patent No.: US 8,497,471 B2
(45) Date of Patent: *Jul. 30, 2013

(54) MASS SPECTROMETRY ASSAY FOR THIOPURINE-S-METHYL TRANSFERASE ACTIVITY AND PRODUCTS GENERATED THEREBY

(75) Inventors: William F. Haddon, Kelseyville, CA (US); Nigel J. Clarke, Oceanside, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/232,861

(22) Filed: Sep. 14, 2011

(65) Prior Publication Data

US 2012/0003676 A1  Jan. 5, 2012

Related U.S. Application Data

(63) Continuation of application No. 12/336,499, filed on Dec. 16, 2008, now Pat. No. 8,039,794.

(51) Int. Cl.
*B01D 59/44* (2006.01)
(52) U.S. Cl.
CPC ..................................... *B01D 59/44* (2013.01)
USPC ................. 250/282; 250/288; 435/6; 435/15; 435/193
(58) Field of Classification Search
USPC ................. 250/282, 288, 281; 435/6.11, 6.16, 435/6, 15, 91.1, 91.2, 193
See application file for complete search history.

(56) References Cited

U.S. PATENT DOCUMENTS

| | | | |
|---|---|---|---|
| 5,143,854 | A | 9/1992 | Pirrung et al. |
| 5,539,517 | A | 7/1996 | Cabib et al. |
| 5,578,832 | A | 11/1996 | Trulson et al. |
| 5,772,874 | A | 6/1998 | Quinn et al. |
| 5,789,216 | A | 8/1998 | Lou et al. |
| 5,790,727 | A | 8/1998 | Dhadwal et al. |
| 5,795,469 | A | 8/1998 | Quinn et al. |
| 5,846,708 | A | 12/1998 | Hollis et al. |
| 5,856,095 | A | 1/1999 | Evans et al. |
| 5,861,242 | A | 1/1999 | Chee et al. |
| 5,880,473 | A | 3/1999 | Ginestet |
| 5,919,368 | A | 7/1999 | Quinn et al. |

(Continued)

FOREIGN PATENT DOCUMENTS

| | | |
|---|---|---|
| EP | 1 285 085 | 1/2008 |
| WO | WO-95/27789 | 10/1995 |

(Continued)

OTHER PUBLICATIONS

Alves, et al, Characterization of three new VNTR alleles in the promoter region of the TPMT gene, Hum Mutat, (2000), 15(1):121.

(Continued)

*Primary Examiner* — Kiet T Nguyen
(74) *Attorney, Agent, or Firm* — Foley & Lardner LLP (57) ABSTRACT

Methods are described for measuring the amount of a methylation TPMT enzyme product in a sample. More specifically, mass spectrometric methods are described for detecting and quantifying 6-MMP or isotopically labeled 6-MMP in a test sample utilizing mass spectrometric techniques and for using such methods to determine the activity of TPMT enzyme that is present in a sample.

14 Claims, 2 Drawing Sheets

U.S. PATENT DOCUMENTS

| | | | |
|---|---|---|---|
| 5,922,617 | A | 7/1999 | Wang et al. |
| 5,943,129 | A | 8/1999 | Hoyt et al. |
| 5,968,367 | A | 10/1999 | Quinn et al. |
| 6,049,380 | A | 4/2000 | Goodwin et al. |
| 6,054,279 | A | 4/2000 | Nadeau et al. |
| 6,055,325 | A | 4/2000 | Garini et al. |
| 6,066,459 | A | 5/2000 | Garini et al. |
| 6,083,697 | A | 7/2000 | Beecher et al. |
| 6,107,623 | A | 8/2000 | Bateman et al. |
| 6,124,137 | A | 9/2000 | Hutchens et al. |
| 6,140,044 | A | 10/2000 | Besemer et al. |
| 6,143,495 | A | 11/2000 | Lizardi et al. |
| 6,183,698 | B1 | 2/2001 | Vassiliou et al. |
| 6,191,425 | B1 | 2/2001 | Imai |
| 6,204,500 | B1 | 3/2001 | Whitehouse et al. |
| 6,252,664 | B1 | 6/2001 | Barbera-Guillem |
| 6,261,776 | B1 | 7/2001 | Pirrung et al. |
| 6,268,144 | B1 | 7/2001 | Koster |
| 6,287,850 | B1 | 9/2001 | Besemer et al. |
| 6,291,183 | B1 | 9/2001 | Pirrung et al. |
| 6,294,331 | B1 | 9/2001 | Ried et al. |
| 6,297,018 | B1 | 10/2001 | French et al. |
| 6,306,643 | B1 | 10/2001 | Gentalen et al. |
| 6,308,170 | B1 | 10/2001 | Balaban |
| 6,887,665 | B2 | 5/2005 | Trulson et al. |
| 6,977,143 | B1 | 12/2005 | Caulfield et al. |
| 7,452,689 | B2 | 11/2008 | O'Brien et al. |
| 7,473,560 | B2 | 1/2009 | Soldin |
| 7,727,737 | B2 | 6/2010 | O'Brien et al. |
| 7,919,251 | B2 * | 4/2011 | Sanderson et al. ........... 435/6.16 |
| 7,972,780 | B2 * | 7/2011 | Duley et al. .................. 435/6.11 |
| 2001/0007747 | A1 | 7/2001 | Bochkariov et al. |
| 2001/0018514 | A1 | 8/2001 | McGall et al. |
| 2004/0038269 | A1 | 2/2004 | Birnboim |
| 2006/0134663 | A1 | 6/2006 | Harkin et al. |
| 2006/0216726 | A1 | 9/2006 | Dervieux |
| 2006/0263840 | A1 | 11/2006 | O'Brien et al. |

FOREIGN PATENT DOCUMENTS

| | | |
|---|---|---|
| WO | WO-97/07201 | 2/1997 |
| WO | WO-99/60163 | 11/1999 |
| WO | WO-00/09650 A1 | 2/2000 |
| WO | WO-00/26412 A1 | 5/2000 |
| WO | WO-00/42222 A2 | 7/2000 |
| WO | WO-00/47600 A1 | 8/2000 |
| WO | WO-01/01144 A2 | 1/2001 |
| WO | WO-01/46467 A2 | 6/2001 |
| WO | WO-02/059354 | 8/2002 |
| WO | WO-02/061121 | 8/2002 |
| WO | WO-03/104251 A2 | 12/2003 |

OTHER PUBLICATIONS

Alves, et al, Influence of the variable number of tandem repeats located in the promoter region of the thiopurine methyltransferase gene on enzymatic activity, Clin Pharmacol Ther, (2001), 70:165-174.
Anglicheau, D., et al., Thiopurine methyltransferase activity: new conditions for reversed-phase high-performance liquid chromatographic assay without extraction and genotypic-phenotypic correlation, J. Chromatogr. B., 773:119-27 (2002).
Avseekno et al, Immobilization of proteins in immunochemical microarrays fabricated by electrospray deposition, Anal Chem 15; 73(24): 6047-52 2001.
Bartolucci, et al., Liquid chromatography tandem mass spectrometric quantitation of sulfamethazine and its metabolites: direct analysis of swine urine by triple quadrupole and by ion trap mass spectrometry, Rapid Commun. Mass Spectrom, 14:967-73 (2000).
Bosch et al, Genetic Polymorphisms of Drug-Metabolising Enzymes and Drug Transporters in the Chemotherapeutic Treatment of Cancer. Clinical Pharmacokinetics, 2006, vol. 45, No. 3, pp. 253-285.
Breen, D., et al., Pharmacogenetic Assocation With Adverse Drug Reactions to Azathioprine Immunosuppressive Therapy Following Liver Transplantation, Liver Transplantation, 11:826-33 (2005).
Caruthers et al, New Chemical Methods for Synthesizing Polynucleotides, Nucleic Acids Res., Symp. Ser., 215-233 1980.
Chen, et al, Fluorescence polarization in homogeneous nucleic acid analysis, Genome Res, (1999), 9(5):492-498.
Coulthard, et al, Recent advances in the pharmacogenomics of thiopurine methyltransferase, (2001), Pharmacogenomics J, 1(4):254-261.
Coulthard, S.A. et al., The Clinical Impact of Thiopurine Methyltransferase Polymorphisms on Thiopurine Treatment. Nucleosides, Nucleotides & Nucleic Acids, 2004, vol. 23, No (8-9):1385-1391.
Extended European Search Report dated May 18, 2011 in application EP 08826993.
Fabre, et al, The impact of thiopurine S-methyltransferase polymorphisms on azathiopurine dose 1 year after renal transplantation, (2004), Off J Euro Soc Organ Trans, 17(9):531-539.
Fahy et al., Multiplex fluorescence-based primer extension method for quantative mutation analysis of mitrochondrial DNA and its diagnostic application for Alzheimer 19s disease, Nucleic Acid Research 25:3102-3109, 1997.
Fessing, et al, Molecular cloning and functional characterization of the cDNA encoding the murine thiopurine S-methyltransferase (TPMT), (1998), FEBS Lett, 424(3):143-145.
Ford, et al., Whole-blood thiopurine S-methyltransferase activity with genotype concordance: a new, simplified phenotyping assay, Ann. Clin. Biochem., 43:354-60 (2006).
Haddon, et al., Metastable ion characteristics. VII. Collision-induced metastables, J. Am. Chem. Soc, 90:4745-46 (1968).
Hafner et al., Biotechniques Apr. 2001;30(4):852-6, 858, 860 passim.
Huang, Detection of multiple proteins in an antibody-based protein microarray system, Immunol Methods, 1; 255(1-2): 1-13 2001.
International Preliminary Report on Patentability dated Feb. 2, 2009 in application PCT/NZ2007/000329.
International Search Report dated Feb. 17, 2010 for PCT Patent Application No. PCT/US2009/067923.
International Search Report dated Apr. 18, 2008 for PCT Application No. PCT/NZ2007/000329.
International Search Report dated Nov. 27, 2008 in application PCT/NZ2008/000197.
International Search Report dated Feb. 17, 2010 in application PCT/US2009/067923.
International Search Report dated Apr. 18, 2008 in application PCT/NZ2007/000329.
Jemal, High-throughput quantitative bioanalysis by LC/MS/MS, Biomedical Chromatography, 14:422-429, 2000.
Kalsi, K., et al., HPLC/Tandem Ion Trap Mass Detector Methods for Determination of Inosine Monophosphate Dehydrogenase (IMPDH) and Thiopurine Methyltransferase (TPMT), Nucleosides, Nucleotide, and Nucleic Acids, 25:1241-4 (2006).
Karim, et al, Convenient genotyping of six myostatin mutations causing double-muscling in cattle using multiplex oligonucleotide ligation assay, Animal Genetics, (2000), 31:396-399.
Krynetski, et al, Promoter and intronic sequences of the human thiopurine S-methyltransferase (TPMT) gene isolated from a human Pac1 genomic library, Pharm Res, (1997), 14(12):1672-1678.
Kwok, Methods for Genotyping Single Nucleotide Polymorphisms, Annu Rev Genomics Hum Genet, 2:235-258 (2001).
Lahiri, et al, A rapid non-enzymatic method for the preparation of HMW DNA from blood for RFLP studies, Nucleic Acids Res, (1991), 19(19):5444.
Lindblad-Toh et al., Large-scale discovery and genotyping of single-nucleotide polymorphisms in the mouse. Nature Genet. Apr. 2000;24(4)pp. 381-386.
Lindqvist, et al, Explaining TPMT genotype/phenotype discrepency by haplotyping of TPMT*3A and identification of a novel sequence variant, TPMT*23, Pharmacogenet Genomics, (2007), 17:891-895.
Lipshutz et al, High density synthetic oligonucleotide arrays. Nature Genetics 1999, 21:20-24.
Marinaki, et al, Genetic determinants of the thiopurine methyltransferase intermediate activity phenotype in British Asians and Caucasians, (2003), Pharmacogenetics, 13(2):97-105.
Merchant and Weinberger, Recent advancements in surface-enhanced laser desorption/ionization-time of flight-mass spectrometry. Electrophoresis 21: 1164-67 (2000).

Pegram et al, t(3;11) translocation in treatment-related acute myeloid leukemia fuses MLL with the GMPS (guanosine 5-prime monophosphate synthetase) gene. Blood 96: 4360-4362, 2000.

Polson et al., Optimization of protein precipitation based upon effectiveness of protein removal and ionization effect in liquid chromatography-tandem mass spectrometry, Journal of Chromatography B 785:263-275 (2003).

Present et al, 6-Mercaptopurine in the management of inflammatory bowel disease: short- and long-term toxicity, Annals of Internal Medicine 111: 641-649 1989).

Reich DE et al, Linkage disequilibrium in the human genome, Nature 2001, 411: 199-204. 2001.

Robb et al., Atmospheric Pressure Photoionization: An Ionization Method for Liquid Chromatography-Mass Spectrometry. Anal. Chem. 72(15):3653-3659 (2000).

Roberts et al, Trinucleotide repeat variants in the promoter of thiopurine s-methyltransferase gene of patients exhibiting ultra-high enzyme activity, Pharmacogenetics and Genomic, (2008), 18(5):434-438.

Roberts, et al, IMPDH1 promoter mutations in a patient exhibiting azathioprine resistance, Pharmacogenomics J, (2007), 7(5):312-317.

Rubin et al (1994. Pathology (Second Edition) Philadelphia: J.B. Lippincott Company.

Saiki, Amplification of Genomic DNA, in PCR Protocols, Innis et al., Eds., Academic Press, San Diego, CA 1990, pp. 13-20.

Saxena, et al, Short nucleotide polymorphic insertions in the MCL-1 promoter affect gene expression, Cancer Lett, (2007), 251:114-131.

Schaeffeler, et al, Three novel thiopurine S-methyltransferase allelic variants (TPMT*20, *21, *22)-association with decreased enzyme function, Hum Mutat, (2006), 921:1-8.

Schweitzer et al, Measuring proteins on microarrays, Curr Opin Biotechno, 13(1): 14-9 2002.

Sies, et al, Measurement of thiopurine methyl transferase activity guides dose-initiation and prevents toxicity from azathioprine, NZ Med J, (2005), 118(1210): 1-7.

Spek, et al, Unique distance- and DNA-turn-dependent interactions in the human protien C gene promoter confer submaximal transcription activity, Biochem J, (1999), 340:513-518.

Spire-Vayron de la Moureyre et al, Characterization of a variable number of tandem repeat region in the thiopurine s-methyltransferase gene promoter, Pharmacogenetics, (1999), 9(2):189-198.

Spire-Vayron de la Moureyre et al, Genotypic and phenotypic analysis of the polymorphic thiopurine S-methyltransferase gene (TPMT) in a European population, (1998), Brit J Pharmocology, 124(4):879-887.

Syvanen et al, Approaches for analyzing human mutations and nucleotide sequence variation: a report from the Seventh International Mutation Detection meeting, 2003. Hum Mutat 23,401-405. 2004.

UCSD Genome Browser (http://www.genome.ucsc.edu) (Jul. 2003 Assembly).

US Notice of Allowance dated Jun. 15, 2011 in U.S. Appl. No. 12/336,499.

US Notice of Allowance dated Jul. 30, 2010 in U.S. Appl. No. 11/566,174.

US Office Action dated Jun. 3, 2010 in U.S. Appl. No. 11/566,174.

US Office Action dated May 4, 2009 for U.S. Appl. No. 11/566,174.

US Office Action dated Sep. 23, 2009 for U.S. Appl. No. 11/566,174.

Wan, W., et al., Rapid screening for S-adenosylmethionine-dependent methylation products by enzyme-transferred isotope patterns analysis, Rapid Comm. Mass Spectrom., 18:319-24 (2004).

Wang, et al, Thiopurine S-methyltransferase pharmacogenetics: insights, challenges and future directions, Oncogene, (2006), 25:1629-1638.

Weinshilboum, R., et al., Human Erythrocyte Thiol Methyltransferase: Radiochemical Microassay and Biochemical Properties, Clinica Chemica Acta, 97:59-71 (1979).

Wright et al, Proteinchip surface enhanced laser desorption/ionization (SELDI) mass spectrometry: a novel protein biochip technology for detection of prostate cancer biomarkers in complex protein mixtures, Prostate Cancer and Prostatic Diseases, 2:264-76, (1999).

Yan, et al, Thiopurine methyltransferase polymorphic tandem repeat: genotype-phenotype correlation analysis, Clin Pharmacol Ther, (2000), 68:210-219.

Zimmer et al., Comparison of turbulent-flow chromatography with automated solid-phase extraction in 96-well plates and liquid-liquid extraction used as plasma sample preparation techniques for liquid chromatography-tandem mass spectrometry. J Chromatogr A, 854: 23-35 (1999).

GenBank:AC104472, Mar. 2003.

GenBank:AL589723.7, Apr. 2001.

Office Action dated Feb. 28, 2012 for CN Application No. 200880110595.9.

US Office Action dated Mar. 20, 2012 in U.S. Appl. No. 12/514,075.

* cited by examiner

MASS SPECTROMETRY ASSAY FOR THIOPURINE-S-METHYL TRANSFERASE ACTIVITY AND PRODUCTS GENERATED THEREBY

CROSS-REFERENCE TO RELATED PATENT APPLICATIONS

This application claims priority to U.S. application Ser. No. 12/336,499 filed Dec. 16, 2008, which is incorporated herein by reference in its entirety including all figures and tables.

FIELD OF THE INVENTION

The invention relates to the measurement of thiopurine-S-methyl transferase (TPMT) activity. In a particular aspect, the invention relates to methods for measurement of thiopurine-S-methyl transferase (TMPT) activity by HPLC-tandem mass spectrometry.

BACKGROUND OF THE INVENTION

The following description of the background of the invention is provided simply as an aid in understanding the invention and is not admitted to describe or constitute prior art to the invention.

6-Mercaptopurine (6-MP) or its pro-drug azathioprine (Imuran) is an immune system suppressant that is widely used to treat Inflammatory Bowel Disease (IBD), Ulcerative Colitis (UC), Crohn's Disease, Lupus, and in some cases, Rheumatoid Arthritis. In addition, Imuran is widely used to minimize organ rejection following transplants, especially of the kidneys. In 1953, 6-MP was introduced as a novel medication to induce remission in children with Acute Lymphocytic Leukemia (ALL). Prior to the introduction of 6-MP, ALL had a 100% fatality rate. Less commonly, a closely related purine, 6-thioguarine, is used instead of 6-MP.

Thiopurine-S-methyltransferase, TPMT enzyme, is a key enzyme in the pathway which converts 6-MP to the active nucleotide form. The gene for TPMT is polymorphic in all populations and gives the classic tri-modal distribution of TPMT activity. About 1 in 300-500 patients will be homozygous for a mutation which leads to rapid proteolytic degradation of TPMT. Thus, there may be homozygous, heterozygous, and wild-type individuals in a population. The approximate distribution is 0.3%, 11%, and 89%, respectively, in a random sampling of the general public. For homozygous patients, where TPMT enzyme has nominally zero activity, extraordinary high levels of the bioactive nucleotides (6-thioguaninenucleotides) are produced. In such individuals, excessive, and potentially lethal, immunosuppression can occur. These patients cannot receive 6-MP therapy safely at any dosage and it is important to identify them prior to initiating 6-MP therapy. Heterozygous individuals comprise about 9-11% of the population. For these patients, the physician typically reduces the dosage of 6-MP by about 50%.

A very small number of wild-type patients will have very high levels of TPMT. This is potentially problematic because early in the metabolic pathway, TPMT acts on the substrate 6-MP to form the potentially toxic metabolic product 6-methylmercaptopurine (6-MMP). Thus, an individual with very low TPMT produces excessively high levels of bioactive nucleotides, whereas a patient with very high TPMT produces excessive 6-MMP and may be at risk for hepatoxicity.

To achieve optimal patient care, it may be desirable to know a patient's level of activity of TPMT enzyme prior to initiating Imuran therapy.

Various methods for measuring TPMT methylation products in a sample have been reported. Various methods have further reported use of these methods to determine TPMT enzyme activity in a sample. For example, Weinshilboum, R., et al., *Clinica Chemica Acta*, 1979, 97:59-71 reports using a HPLC-radioassay to detect TPMT enzyme products and to determine enzyme activity; Wan, W., et al., *Rapid Comm. Mass Spectrom.* 2004, 18:319-24, reports using MALDI-TOF mass spectrometry to detect TPMT generated 6-MMP and isotopically labeled 6-MMP in bacterial cell lysates; Kalsi, K., et al., *Nucleosides, Nucleotides, and Nucleic Acids* 2006, 25:1241-4, reports measuring TPMT enzyme activity in isolated red blood cells through detection of TPMT generated 6-MMP with ion trap mass spectrometry; Anglicheau, D., et al., *J. Chromatogr. B.* 2002, 773:119-27, reports utilization of HPLC with UV detection of 6-MMP to determine TPMT enzyme activity from isolated red blood cells; Breen, D., et al., *Liver Transplantation* 2005, 11:826-33, reports utilization of tandem mass spectrometry to detect TPMT generated 6-MMP from isolated red blood cells; and O'Brian, et al., U.S. patent application Ser. No. 11/370,581 (filed Mar. 8, 2006), reports utilization of tandem mass spectrometry to detect TPMT generated 6-MMP from isolated red blood cells through monitoring the reaction of a precursor ion at a mass to charge ratio of 165 to a fragment ion at a mass to charge ratio of 150.

SUMMARY OF THE INVENTION

The present invention provides methods for detecting the amount of 6-MMP in a sample and for measuring thiopurine-S-methyltransferase (TPMT) activity in a sample by mass spectrometry, including tandem mass spectrometry. Preferably, the methods of the invention include high performance liquid chromatography.

In one aspect, methods are provided for determining the amount of 6-methylmercaptopurine (6-MMP) in a sample with tandem mass spectrometry. Methods of this aspect include: (a) ionizing 6-MMP, purified by solid phase extraction (SPE) from the sample, under conditions suitable to produce one or more ions detectable by mass spectrometry; (b) determining the amount of one or more ions by tandem mass spectrometry; and (c) using the amount of the one or more ions to determine the amount of 6-MMP in the sample. In some preferred embodiments, the SPE is preferably conducted with on-line processing. In some embodiments, the sample comprises red blood cells; preferably the sample comprises whole blood. In some embodiments, SPE comprises turbulent-flow liquid chromatography (TFLC). In some embodiments, 6-MMP purified by SPE is further purified by high performance liquid chromatography (HPLC); preferably with on-line processing.

In some embodiments, the ions detected by tandem mass spectrometry are selected from the group consisting of ions with a mass to charge ratio of $167.1\pm0.5$, $152.1\pm0.5$, $134.1\pm0.5$, $126.1\pm0.5$, $125.1\pm0.5$, $119.1\pm0.5$, $99.1\pm0.5$, $98.1\pm0.5$, and $92.1\pm0.5$; preferably the ions detected by mass spectrometry are a precursor ion with a mass to charge ratio of $167.1\pm0.5$, and one or more fragment ions selected from the group consisting of ions with mass to charge ratios of $152.1\pm0.5$, $134.1\pm0.5$, $126.1\pm0.5$, $125.1\pm0.5$, $119.1\pm0.5$, $99.1\pm0.5$, $98.1\pm0.5$, and $92.1\pm0.5$; preferably, one of the one or more fragment ions is an ion with a mass to charge ratio of $125.1\pm0.5$. In some embodiments, the step of determining the amount of 6-MMP in a sample comprises comparison to an internal standard. In some embodiments, the internal standard is an isotopically labeled 6-MMP; preferably $d_3$-6-MMP.

The above listed features may be combined without limitation for use in methods of the present invention.

In other embodiments of this aspect, methods are provided for determining the amount of 6-methylmercaptopurine (6-MMP) in a sample with tandem mass spectrometry. These methods include: (a) ionizing 6-MMP from the sample under conditions suitable to produce one or more ions detectable by mass spectrometry; wherein the one or more ions detectable by mass spectrometry are selected from the group consisting of ions with mass to charge ratios of 167.1±0.5, 152.1±0.5, 134.1±0.5, 126.1±0.5, 125.1±0.5, 119.1±0.5, 99.1±0.5, 98.1±0.5, and 92.1±0.5; (b) determining the amount of one or more ions by tandem mass spectrometry, and (c) using the amount of the one or more ions to determine the amount of 6-MMP in the sample. In some embodiments, the sample comprises red blood cells; preferably the sample is whole blood. In some embodiments, 6-MMP in the sample has been purified by high performance liquid chromatography (HPLC) prior to ionization; preferably with on-line processing. In some embodiments, 6-MMP in the sample has been purified by solid phase extraction (SPE) prior to ionization; preferably SPE comprises turbulent flow liquid chromatography (TFLC) prior to ionization, preferably with on-line processing. In some embodiments, the one or more ions detected by mass spectrometry comprise a precursor ion with a mass to charge ratio of 167.1±0.5, and one or more fragment ions selected from the group consisting of ions with mass to charge ratios of 152.1±0.5, 134.1±0.5, 126.1±0.5, 125.1±0.5, 119.1±0.5, 99.1±0.5, 98.1±0.5, and 92.1±0.5; preferably, one of the one or more fragment ion is an ion with a mass to charge ratio of 125.1±0.5. In some embodiments, the amount of one or more ions determined by mass spectrometry is related to the presence or amount of 6-MMP in the sample by comparison to an internal standard. In some embodiments, the internal standard is an isotopically labeled 6-MMP; preferably $d_3$-6-MMP.

The above listed features may be combined without limitation for use in methods of the present invention.

In other embodiments of this aspect, methods are provided for determining the amount of isotopically labeled 6-methylmercaptopurine (6-MMP) in a sample with tandem mass spectrometry. These methods include: (a) ionizing isotopically labeled 6-MMP from the sample under conditions suitable to produce one or more ions detectable by mass spectrometry; (b) determining the amount of one or more ions by tandem mass spectrometry; and (c) using the amount of the one or more ions to determine the amount of isotopically labeled 6-MMP in the sample; preferably the isotopically labeled 6-MMP is $d_3$-6-MMP, and the one or more ions are selected from the group consisting of ions with mass to charge ratios of 170.1±0.5, 152.1±0.5, 137.1±0.5, 136.1±0.5, 126.1±0.5, 125.1±0.5, 119.1±0.5, 99.1±0.5, 98.1±0.5, and 92.1±0.5; preferably the ions detected by mass spectrometry comprise a precursor ion with a mass to charge ratio of 170.1±0.5, and one or more fragment ions selected from the group of ions with mass to charge ratios of 152.1±0.5, 137.1±0.5, 136.1±0.5, 126.1±0.5, 125.1±0.5, 119.1±0.5, 99.1±0.5, 98.1±0.5, and 92.1±0.5; preferably, one of the one or more fragment ions is an ion with a mass to charge ratio of 125.1±0.5. In some embodiments, the methods have a limit of quantitation within the range of 0.8 ng/mL to 10 ng/mL, inclusive. In some embodiments, the sample comprises red blood cells; preferably the sample comprises whole blood. In some embodiments, isotopically labeled 6-MMP in the sample has been purified by high performance liquid chromatography (HPLC) prior to ionization, preferably with on-line processing. In some embodiments, isotopically labeled 6-MMP in the sample has been purified by solid phase extraction (SPE) prior to ionization; preferably SPE comprises turbulent flow liquid chromatography (TFLC) prior to ionization; preferably with on-line processing. In some embodiments, the step of relating the amount of one or more ions detected by tandem mass spectrometry to the amount of isotopically labeled 6-MMP in the sample comprises comparison to an internal standard; preferably the internal standard comprises 6-MMP. In some embodiments, the methods have a lower limit of quantitation within the range of 0.8 ng/mL and 10 ng/mL, inclusive. The features of the embodiments listed above may be combined without limitation for use in methods of the present invention.

In a second aspect, methods are provided for determining thiopurine-S-methyl transferase (TPMT) activity in a sample by mass spectrometry. The methods include: (a) incubating for a specified period of time the sample with an isotopically labeled substrate for TPMT under conditions suitable for the generation of an isotopically labeled 6-methylmercaptopurine (6-MMP) by TPMT in the sample, thereby forming an incubated sample; (b) ionizing isotopically labeled 6-MMP from the incubated sample under conditions suitable to produce one or more ions detectable by mass spectrometry; (c) determining the amount of one or more ions by mass spectrometry; (d) using the amount of the one or more ions to determine the amount of isotopically labeled 6-MMP in the incubated sample; and (e) using the amount of isotopically labeled 6-MMP in the incubated sample to calculate TPMT activity in the sample. In some embodiments, incubating comprises incubating the sample in the presence of isotopically labeled S-adenosylmethionine (SAM); preferably $d_3$-S-adenosylmethionine ($d_3$-SAM). In preferred embodiments, the isotopically labeled 6-MMP is $d_3$-6-methylmercaptopurine ($d_3$-6-MMP). In some related embodiments, one of the ions detectable by mass spectrometry is an ion with a mass to charge ratio of 170.1±0.5. In some embodiments, the sample comprises red blood cells; preferably the sample comprises whole blood. In some embodiments, mass spectrometry is tandem mass spectrometry. In preferred related embodiments, the one or more ions detectable by mass spectrometry comprise a precursor ion with a mass to charge ratio of 170.1±0.5, and one or more fragment ions selected from the group of ions with mass to charge ratios of 152.1±0.5, 137.1±0.5, 136.1±0.5, 126.1±0.5, 125.1±0.5, 119.1±0.5, 99.1±0.5, 98.1±0.5, and 92.1±0.5; preferably one of the one or more fragment ions is an ion with a mass charge ratio of 125.1±0.5. In some embodiments, isotopically labeled 6-MMP from the incubated sample has been purified with liquid chromatography (LC) prior to ionization, preferably with on-line processing. In preferred embodiments, liquid chromatography comprises high performance liquid chromatography (HPLC). In some embodiments, isotopically labeled 6-MMP from the incubated sample has been purified with solid phase extraction (SPE) prior to ionization; in preferred embodiments, SPE comprises turbulent flow liquid chromatography (TFLC); preferably with on-line processing. In some embodiments, the amount of one or more ions detected by mass spectrometry is related to the presence or amount of isotopically labeled 6-MMP in the incubation sample by comparison to an internal standard; preferably the internal standard is 6-MMP. The features of the embodiments listed above may be combined without limitation for use in methods of the present invention.

In other embodiments of this aspect, methods are provided for measuring thiopurine-S-methyl transferase (TPMT) activity in a sample including: (a) incubating for a specified period of time the sample under conditions suitable for the generation of 6-methylmercaptopurine (6-MMP) by TPMT in the sample, thereby forming an incubated sample; (b) ionizing said 6-MMP, purified by solid phase extraction (SPE) from the incubated sample, under conditions suitable to produce one or more ions detectable by mass spectrometry; (c) determining the amount of one or more ions by tandem mass spectrometry; (d) using the amount of the one or more ions to determine the amount of 6-MMP in the incubated sample; and (e) using the amount of 6-MMP in the incubated sample to calculate TPMT activity in the sample. In some embodiments, the sample comprises red blood cells: preferably the sample comprises whole blood. In some embodiments, incubating comprises incubating the sample in the presence of 6-mercaptopurine (6-MP) and S-adenosylmethionine (SAM). In some embodiments, the one or more ions comprise ions selected from the group of ions with mass to charge ratios of $167.1 \pm 0.5$, $152.1 \pm 0.5$, $134.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; preferably the one or more ions comprises a parent ion with a mass to charge ratio of $167.1 \pm 0.5$, and one or more fragment ions selected from the group consisting of ions with mass to charge ratios of $152.1 \pm 0.5$, $134.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; preferably one of the one or more fragment ions is an ion with a mass to charge ratio of $125.1 \pm 0.5$. In other embodiments, incubating comprises incubating the sample in the presence of an isotopically labeled substrate for TPMT. In some related embodiments, the isotopically labeled substrate for TPMT is an isotopically labeled S-adenosylmethionine (SAM); preferably $d_3$-S-adenosylmethionine ($d_3$-SAM). In some related embodiments, the one or more ions comprise ions selected from the group of ions with mass to charge ratios of $170.1 \pm 0.5$, $152.1 \pm 0.5$, $137.1 \pm 0.5$, $136.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; preferably the one or more ions comprise a precursor ion with a mass to charge ratio of $170.1 \pm 0.5$, and one or more fragment ions selected from the group of ions with mass to charge ratios of $152.1 \pm 0.5$, $137.1 \pm 0.5$, $136.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; preferably, one of the one or more fragment ions is an ion with a mass to charge ratio of $125.1 \pm 0.5$. In some embodiments, 6-MMP in the incubation sample has been purified with liquid chromatography (LC) prior to ionization: preferably with on-line processing. In some embodiments, LC comprises high performance liquid chromatography (HPLC). In preferred embodiments, SPE comprises turbulent flow liquid chromatography; preferably with on-line processing. The features of the embodiments listed above may be combined without limitation for use in methods of the present invention.

In other embodiments of this aspect, methods are provided for measuring thiopurine-S-methyl transferase (TPMT) activity in a sample using tandem mass spectrometry. These methods include: (a) incubating for a specified period of time the sample with an isotopically labeled substrate for TPMT under conditions suitable for the generation of isotopically labeled 6-methylmercaptopurine (6-MMP) by TPMT in the sample, thereby forming an incubated sample; (b) purifying the isotopically labeled 6-MMP in the incubated sample by solid phase extraction (SPE); (c) further purifying the isotopically labeled 6-MMP by liquid chromatography (LC); (d) ionizing the purified isotopically labeled 6-MMP under conditions suitable to produce one or more ions detectable by tandem mass spectrometry; (e) determining the amount of one or more ions by tandem mass spectrometry; wherein the one or more ions are selected from the group of ions consisting of ions with mass to charge ratios of $170.1 \pm 0.5$, $152.1 \pm 0.5$, $137.1 \pm 0.5$, $136.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; (f) using the amount of the one or more ions to determine the amount of isotopically labeled 6-MMP in the incubated sample; and (g) using the amount of 6-MMP in the incubated sample to calculate TPMT activity in the sample. In some embodiments, SPE comprises turbulent flow liquid chromatography (TFLC); preferably with on-line processing. In some embodiments, LC comprises high performance liquid chromatography (HPLC); preferably with on-line processing. In some embodiments, the sample comprises red blood cells; preferably the sample comprises whole blood. In some embodiments, incubating comprises incubating the sample in the presence of an isotopically labeled reagent; preferably the isotopically labeled reagent is an isotopically labeled S-adenosylmethionine (SAM); more preferably the isotopically labeled reagent is $d_3$-S-adenosylmethionine ($d_3$-SAM). In some related embodiments, the one or more ions determined by tandem mass spectrometry comprise a parent ion with a mass to charge ratio of $170.1 \pm 0.5$, and one or more fragment ions selected from the group of ions with mass to charge ratios of $152.1 \pm 0.5$, $137.1 \pm 0.5$, $136.1 \pm 0.5$, $126.1 \pm 0.5$, $125.1 \pm 0.5$, $119.1 \pm 0.5$, $99.1 \pm 0.5$, $98.1 \pm 0.5$, and $92.1 \pm 0.5$; preferably, one of the one or more fragment ions is an ion with a mass to charge ratio of $125.1 \pm 0.5$. The features of the embodiments listed above may be combined without limitation for use in methods of the present invention.

Methods of the present invention may involve the combination of liquid chromatography with mass spectrometry, In preferred embodiments, the liquid chromatography is HPLC. One preferred embodiment utilizes HPLC alone or in combination with one or more purification methods such as for example SPE (e.g., TFLC) and/or protein precipitation and filtration, to purify an analyte in a sample. In these embodiments, at least one purification step and mass spectrometric analysis may be conducted in an on-line fashion. In another preferred embodiment, the mass spectrometry is tandem mass spectrometry (MS/MS).

In certain preferred embodiments of the methods disclosed herein, mass spectrometry is performed in positive ion mode. Alternatively, mass spectrometry is performed in negative ion mode. Various ionization sources, including for example atmospheric pressure chemical ionization (APCI) or electrospray ionization (ESI), may be used in embodiments of the present invention. In certain preferred embodiments, 6-MMP and/or isotopically labeled 6-MMP is measured using APCI in positive ion mode.

In some preferred embodiments, 6-MMP ions detectable in a mass spectrometer are selected from the group consisting of positive ions with a mass/charge ratio (m/z) of $167.10 \pm 0.50$ and $125.10 \pm 0.50$. In particularly preferred embodiments, a 6-MMP precursor ion has m/z of $167.10 \pm 0.50$, and a fragment ion has m/z of $125.10 \pm 0.50$. Other fragment ions, however may be observed and used in the presented methods. For example, fragment ions for 6-MMP precursor ions may include ions with a mass to charge ratio of $152.1 \pm 0.5$, $134.1 \pm 0.5$, $126.1 \pm 0.5$, $125.1 \pm 0.5$, $119.1 \pm 0.5$, $99.1 \pm 0.5$, $98.1 \pm 0.5$, or $92.1 \pm 0.5$.

In other preferred embodiments, isotopically labeled 6-MMP ions detectable in a mass spectrometer are selected from the group consisting of positive ions with a mass/charge ratio (m/z) of $170.10 \pm 0.50$ and $125.10 \pm 0.50$. In particularly preferred embodiments, an isotopically labeled 6-MMP precursor ion has m/z of $170.10 \pm 0.50$, and a fragment ion has m/z of 125.10±0.50. Other fragment ions, however may be observed and used in the presented methods. For example, fragment ions for isotopically labeled 6-MMP precursor ions may include ions with a mass to charge ratio of 152.1±0.5, 137.1±0.5, 136.1±0.5, 126.1±0.5, 125.1±0.5, 119.1±0.5, 99.1±0.5, 98.1±0.5, and 92.1±0.5.

In preferred embodiments, a separately detectable internal standard is provided in the sample, the amount of which is also determined in the sample. In these embodiments, all or a portion of both the analyte of interest and the internal standard present in the sample is ionized to produce a plurality of ions detectable in a mass spectrometer, and one or more ions produced from each are detected by mass spectrometry. In these embodiments, the presence or amount of ions generated from the analyte of interest may be related to the presence of amount of analyte of interest in the sample.

For methods of the present invention where an analyte of interest is 6-MMP, a preferred internal standard is isotopically labeled 6-MMP. In these embodiments, the internal standard ions detectable in a mass spectrometer are selected from the group consisting of positive ions with m/z of 170.10±0.50 and 125.10±0.50; particularly, an internal standard precursor ion has m/z of 170.10±0.50; and an internal standard fragment ion has m/z of 125.10±0.50.

For methods of the present invention where an analyte of interest is isotopically labeled 6-MMP, a preferred internal standard is 6-MMP. In these embodiments, the internal standard ions detectable in a mass spectrometer are selected from the group consisting of positive ions with m/z of 167.10±0.50 and 125.10±0.50; particularly, an internal standard precursor ion has m/z of 167.10±0.50; and an internal standard fragment ion has m/z of 125.10±0.50.

In certain preferred embodiments, the lower limit of quantitation (LLOQ) of 6-MMP, or isotopically labeled 6-MMP, is within the range of 3.2 ng/mL to 15 ng/mL, inclusive; preferably within the range of 3.2 ng/mL to 10 ng/mL, inclusive; preferably within the range of 3.2 ng/mL to 5.0 ng/mL, inclusive; preferably about 3.2 ng/mL.

In certain preferred embodiments where a measured amount of 6-MMP, or isotopically labeled 6-MMP, is used to determine TPMT enzyme activity, the LLOQ of TMPT activity for samples with a hematocrit of about 0.4 is within the range of about 1.31 to 6.14 nmole 6-MMP/hour/mL RBC, inclusive; preferably within the range of about 1.31 to 4.09 nmole 6-MMP/hour/mL RBC, inclusive; preferably within the range of about 1.31 to 2.05 nmole 6-MMP/hour/mL RBC, inclusive; preferably about 1.31 nmole 6-MMP/hour/mL RBC.

As used herein, unless otherwise stated, the singular forms "a," "an," and "the" include plural reference. Thus, for example, a reference to "a protein" includes a plurality of protein molecules.

As used herein, an "isotopic label" produces a mass shift in the labeled molecule relative to the unlabeled molecule when analyzed by mass spectrometric techniques. Examples of suitable labels include deuterium, $^{13}C$, and $^{15}N$. Deuterium is a useful label because it can potentially produce three mass shifts in a labeled methylation product relative to an unlabeled methylation product. For example, $d_3$-6-MMP has a mass three units higher than 6-MMP. The isotopic label can be incorporated at one or more positions in the molecule and one or more kinds of isotopic labels can be used on the same isotopically labeled molecule.

As used herein, the term "purification" or "purifying" does not refer to removing all materials from the sample other than the analyte(s) of interest. Instead, purification refers to a procedure that enriches the amount of one or more analytes of interest relative to other components in the sample that may interfere with detection of the analyte of interest. Purification of the sample by various means may allow relative reduction of one or more interfering substances, e.g., one or more substances that may or may not interfere with the detection of selected parent or daughter ions by mass spectrometry. Relative reduction as this term is used does not require that any substance, present with the analyte of interest in the material to be purified, is entirely removed by purification.

As used herein, the term "sample" refers to any sample that may contain an analyte of interest. Preferred test samples for use in the present invention are whole blood and red blood cells (RBC).

As used herein, the term "solid phase extraction" or "SPE" refers to a process in which a chemical mixture is separated into components as a result of the affinity of components dissolved or suspended in a solution (i.e., mobile phase) for a solid through or around which the solution is passed (i.e., solid phase). In some instances, as the mobile phase passes through or around the solid phase, undesired components of the mobile phase may be retained by the solid phase resulting in a purification of the analyte in the mobile phase. In other instances, the analyte may be retained by the solid phase, allowing undesired components of the mobile phase to pass through or around the solid phase. In these instances, a second mobile phase is then used to elute the retained analyte off of the solid phase for further processing or analysis.

As used herein, the term "chromatography" refers to a process in which a chemical mixture carried by a liquid or gas is separated into components as a result of differential distribution of the chemical entities as they flow around or over a stationary liquid or solid phase.

As used herein, the term "liquid chromatography" or "LC" means a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Examples of "liquid chromatography" include reverse phase liquid chromatography (RPLC), high performance liquid chromatography (HPLC), and turbulent flow liquid chromatography (TFLC) (sometimes known as high turbulence liquid chromatography (HTLC) or high throughput liquid chromatography).

As used herein, the term "high performance liquid chromatography" or "HPLC" (also sometimes known as "high pressure liquid chromatography") refers to liquid chromatography in which the degree of separation is increased by forcing the mobile phase under pressure through a stationary phase, typically a densely packed column.

As used herein, the term "turbulent flow liquid chromatography" or "TFLC" (sometimes known as high turbulence liquid chromatography (HTLC) or high throughput liquid chromatography) refers to a form of chromatography that utilizes turbulent flow of the material being assayed through the column packing as the basis for performing the separation. TFLC has been applied in the preparation of samples containing two unnamed drugs prior to analysis by mass spectrometry. See, e.g., Zimmer et al., *J Chromatogr A* 854: 23-35 (1999); see also, U.S. Pat. Nos. 5,968,367, 5,919,368, 5,795,469, and 5,772,874, which further explain TFLC. Persons of ordinary skill in the art understand "turbulent flow". When fluid flows slowly and smoothly, the flow is called "laminar flow". For example, fluid moving through an HPLC column at low flow rates is laminar. In laminar flow the motion of the particles of fluid is orderly with particles moving generally in straight lines. At faster velocities, the inertia of the water overcomes fluid frictional forces and turbulent flow results. Fluid not in contact with the irregular boundary "outruns" that which is slowed by friction or deflected by an uneven surface. When a fluid is flowing turbulently, it flows in eddies and whirls (or vortices), with more "drag" than when the flow is laminar. Many references are available for assisting in determining when fluid flow is laminar or turbulent (e.g., *Turbulent Flow Analysis: Measurement and Prediction*, P. S. Bernard & J. M. Wallace, John Wiley & Sons, Inc., (2000); *An Introduction to Turbulent Flow*. Jean Mathieu & Julian Scott, Cambridge University Press (2001)).

As used herein, the term "gas chromatography" or "GC" refers to chromatography in which the sample mixture is vaporized and injected into a stream of carrier gas (as nitrogen or helium) moving through a column containing a stationary phase composed of a liquid or a particulate solid and is separated into its component compounds according to the affinity of the compounds for the stationary phase.

As used herein, the term "large particle column" or "extraction column" refers to a chromatography column containing an average particle diameter greater than about 50 μm. As used in this context, the term "about" means ±10%.

As used herein, the term "analytical column" refers to a chromatography column having sufficient chromatographic plates to effect a separation of materials in a sample that elute from the column sufficient to allow a determination of the presence or amount of an analyte. Such columns are often distinguished from "extraction columns", which have the general purpose of separating or extracting retained material from non-retained materials in order to obtain a purified sample for further analysis. As used in this context, the term "about" means ±10%. In a preferred embodiment the analytical column contains particles of about 4 μm in diameter.

As used herein, the term "on-line" or "inline", for example as used in "on-line automated fashion" or "on-line extraction" refers to a procedure performed without the need for operator intervention. In contrast, the term "off-line" as used herein refers to a procedure requiring manual intervention of an operator. Thus, if samples are subjected to precipitation, and the supernatants are then manually loaded into an autosampler, the precipitation and loading steps are off-line from the subsequent steps. In various embodiments of the methods, one or more steps may be performed in an on-line automated fashion.

As used herein, the term "mass spectrometry" or "MS" refers to an analytical technique to identify compounds by their mass. MS refers to methods of filtering, detecting, and measuring ions based on their mass-to-charge ratio, or "m/z". MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ionizer and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., *Prostate Cancer and Prostatic Diseases* 1999, 2: 264-76; and Merchant and Weinberger, *Electrophoresis* 2000, 21; 1164-67.

As used herein, the term "operating in negative ion mode" refers to those mass spectrometry methods where negative ions are generated and detected. The term "operating in positive ion mode" as used herein, refers to those mass spectrometry methods where positive ions are generated and detected.

As used herein, the term "ionization" or "ionizing" refers to the process of generating an analyte ion having a net electrical charge equal to one or more electron units. Negative ions are those having a net negative charge of one or more electron units, while positive ions are those having a net positive charge of one or more electron units.

As used herein, the term "electron ionization" or "EI" refers to methods in which an analyte of interest in a gaseous or vapor phase interacts with a flow of electrons. Impact of the electrons with the analyte produces analyte ions, which may then be subjected to a mass spectrometry technique.

As used herein, the term "chemical ionization" or "CI" refers to methods in which a reagent gas (e.g. ammonia) is subjected to electron impact, and analyte ions are formed by the interaction of reagent gas ions and analyte molecules.

As used herein, the term "fast atom bombardment" or "FAB" refers to methods in which a beam of high energy atoms (often Xe or Ar) impacts a non-volatile sample, desorbing and ionizing molecules contained in the sample. Test samples are dissolved in a viscous liquid matrix such as glycerol, thioglycerol, m-nitrobenzyl alcohol, 18-crown-6 crown ether, 2-nitrophenyloctyl ether, sulfolane, diethanolamine, and triethanolamine. The choice of an appropriate matrix for a compound or sample is an empirical process.

As used herein, the term "matrix-assisted laser desorption ionization" or "MALDI" refers to methods in which a non-volatile sample is exposed to laser irradiation, which desorbs and ionizes analytes in the sample by various ionization pathways, including photo-ionization, protonation, deprotonation, and cluster decay. For MALDI, the sample is mixed with an energy-absorbing matrix, which facilitates desorption of analyte molecules.

As used herein, the term "surface enhanced laser desorption ionization" or "SELDI" refers to another method in which a non-volatile sample is exposed to laser irradiation, which desorbs and ionizes analytes in the sample by various ionization pathways, including photo-ionization, protonation, deprotonation, and cluster decay. For SELDI, the sample is typically bound to a surface that preferentially retains one or more analytes of interest. As in MALDI, this process may also employ an energy-absorbing material to facilitate ionization.

As used herein, the term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

As used herein, the term "atmospheric pressure chemical ionization" or "APCI," refers to mass spectrometry methods that are similar to ESE however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated $N_2$ gas may be used to improve removal of solvent. The gas-phase ionization in APCI can be more effective than ESI for analyzing less-polar species.

The term "atmospheric pressure photoionization" or "APPI" as used herein refers to the form of mass spectrometry where the mechanism for the photoionization of molecule M is photon absorption and electron ejection to form the molecular ion M+. Because the photon energy typically is just above the ionization potential, the molecular ion is less susceptible to dissociation. In many cases it may be possible to analyze samples without the need for chromatography, thus saving significant time and expense. In the presence of water vapor or protic solvents, the molecular ion can extract H to form MH+. This tends to occur if M has a high proton affinity. This does not affect quantitation accuracy because the sum of M+ and MH+ is constant. Drug compounds in protic solvents are usually observed as MH+, whereas nonpolar compounds such as naphthalene or testosterone usually form M+. See, e.g., Robb et al., *Anal. Chem.* 2000, 72(15): 3653-3659.

As used herein, the term "inductively coupled plasma" or "ICP" refers to methods in which a sample interacts with a partially ionized gas at a sufficiently high temperature such that most elements are atomized and ionized.

As used herein, the term "field desorption" refers to methods in which a non-volatile test sample is placed on an ionization surface, and an intense electric field is used to generate analyte ions.

As used herein, the term "desorption" refers to the removal of an analyte from a surface and/or the entry of an analyte into a gaseous phase. Laser desorption thermal desorption is a technique wherein a sample containing the analyte is thermally desorbed into the gas phase by a laser pulse. The laser hits the back of a specially made 96-well plate with a metal base. The laser pulse heats the base and the heats causes the sample to transfer into the gas phase. The gas phase sample is then drawn into the mass spectrometer.

As used herein, the term "selective ion monitoring" is a detection mode for a mass spectrometric instrument in which only ions within a relatively narrow mass range, typically about one mass unit, are detected.

As used herein, "multiple reaction mode," sometimes known as "selected reaction monitoring," is a detection mode for a mass spectrometric instrument in which a precursor ion is selected and fragmented, and one or more fragment ions of this precursor are selectively detected.

As used herein, the term "lower limit of quantification", "lower limit of quantitation" or LLOQ" refers to the point where measurements become quantitatively meaningful. The analyte response at the LLOQ is identifiable, discrete and reproducible with a relative standard deviation (RSD %) of less than 20% and an accuracy of 85% to 115%.

As used herein, the term "limit of detection" or "LOD" is the point at which the measured value is larger than the uncertainty associated with it. The LOD is the point at which a value is beyond the uncertainty associated with its measurement and is defined as three times the RSD of the mean at the zero concentration.

As used herein, an "amount" of an analyte in a body fluid sample refers generally to an absolute value reflecting the mass of the analyte detectable in volume of sample. However, an amount also contemplates a relative amount in comparison to another analyte amount. For example, an amount of an analyte in a sample can be an amount which is greater than a control or normal level of the analyte normally present in the sample.

The term "about" as used herein in reference to quantitative measurements not including the measurement of the mass of an ion, refers to the indicated value plus or minus 10%. Mass spectrometry instruments can vary slightly in determining the mass of a given analyte. The term "about" in the context of the mass of an ion or the mass/charge ratio of an ion refers to +/−0.50 atomic mass unit.

The summary of the invention described above is non-limiting and other features and advantages of the invention will be apparent from the following detailed description of the invention, and from the claims.

DETAILED DESCRIPTION OF THE INVENTION

Methods are described for measuring the amount of a methylation TPMT enzyme product in a sample. More specifically, mass spectrometric methods are described for detecting and quantifying 6-MMP or isotopically labeled 6-MMP in a test sample. The methods may utilize high turbulence liquid chromatography (HTLC), to perform a purification of selected analytes, combined with methods of mass spectrometry (MS), thereby providing a high-throughput assay system for detecting and quantifying 6-MMP or isotopically labeled 6-MMP in a sample. Methods are also described of measuring TPMT activity by measuring the amount of 6-MMP or isotopically labeled 6-MMP generated in a sample during an incubation period of known duration. The preferred embodiments are particularly well suited for application in large clinical laboratories for automated TPMT activity assay.

The in-vitro TPMT activity assay of the present invention mimics the biochemical methylation reaction in which TPMT converts 6-mercaptopurine (6-MP) and a co-substrate S-adenosylmethionine (SAM) to the metabolite 6-MMP. To determine TPMT enzyme activity in a sample suspected of containing TPMT, 6-MP and SAM are added to the sample and the resulting mixture incubated for a known period of time. Upon completion of the incubation period, the amount of 6-MMP in the sample is directly related to TPMT enzyme activity in the sample. In the instant methods, the amount of 6-MMP in the sample following incubation is determined with tandem mass spectrometry (MS/MS); preferably combined with HTLC. To ensure that the detected 6-MMP is generated during the incubation period, an isotopically labeled reactant, preferably isotopically labeled SAM, most preferably $d_3$-SAM, may be used in place of one of the corresponding non-isotopically labeled reactants in the incubation mixture, resulting in formation of isotopically labeled 6-MMP, preferably $d_3$-6-MMP. The generated methylated product is known to have formed over a defined period of time, from which the TPMT enzyme activity can be calculated.

Suitable test samples for use in methods of the present invention include any test sample that may contain the analyte of interest. In some preferred embodiments, a sample is a biological sample; that is, a sample obtained from any biological source, such as an animal, a cell culture, an organ culture, etc. In certain preferred embodiments, samples are obtained from a mammalian animal, such as a dog, cat, horse, etc. Particularly preferred mammalian animals are primates, most preferably male or female humans. Particularly preferred samples include bodily fluids such as blood, plasma, serum, saliva, cerebrospinal fluid, or tissue samples. Such samples may be obtained, for example, from a patient; that is, a living person, male or female, presenting oneself in a clinical setting for diagnosis, prognosis, or treatment of a disease or condition. The test sample is preferably obtained from a patient, for example, a whole blood specimen or specimen of red blood cells (RBC's). The preferred test sample for the TPMT assay of the present invention is a whole blood specimen, as conducting the assay on a whole blood specimen avoids the need to isolate RBC's prior to measuring TPMT activity. Whole blood specimens of about 3 to 5 mL are preferred. Only about 150 µL of each specimen is required for incubation and determination of enzyme metabolite concentration. The excess specimen volume may be used to determine the specimen's hematocrit in instances when that information is not otherwise available.

The above described incubation may be carried out at any temperature compatible with the preservation of TPMT enzymatic activity, for example between 25° C. and 42° C.; preferably at about 37° C. The reaction may be carried out for any length of time that allows for the accumulation of detectable amounts of the TPMT enzyme product, for example, between 30 and 180 minutes; preferably 60 minutes. At the end of the incubation period, the TPMT enzyme reaction may be terminated by any treatment that considerably reduces or inhibits TPMT activity that is compatible with conditions used to extract the TPMT reaction product and internal standard. Thus, for example, the reaction may be terminated by raising the pH of the sample, e.g., by addition of a buffer with a pH of about 10.0, by addition of an organic solvent, or by rapid heating or cooling of the incubation mixture.

The present invention also contemplates kits for a TPMT enzyme activity assay. A kit for a TPMT enzyme activity assay of the present invention may include a kit comprising the compositions provided herein. For example, a kit may include packaging material and measured amounts of an isotopically labeled SAM, 6-MP, and a methylation product of the non-isotopically labeled TPMT substrates, in amounts sufficient for at least one assay. Typically, the kits will also include instructions recorded in a tangible form (e.g., contained on paper or an electronic medium) for using the packaged reagents for use in a measurement assay for determining the activity of TPMT in a sample. In another embodiment, a kit may include 6-MP, $d_3$-SAM, and 6-MMP.

Calibration and QC pools for use in embodiments of the present invention are preferably prepared using a matrix similar to the intended sample matrix, provided that 6-MP is essentially absent. In preferred embodiments, lysed whole blood (without 6-MP) is used for calibration and QC pools.

TPMT Activity Assay Sample Incubation

As indicated above, test samples suitable for TPMT enzyme activity assays of the present invention are specimens that are suspected of containing TPMT. Preferred samples are whole blood or RBC specimens; more preferably whole blood specimens. Prior to analysis, whole blood or RBC specimens may be stored below room temperature, preferably at about 4° C. However, whole blood or RBC specimens should not be stored below freezing, as this may cause premature cell lysing and release of TPMT contained therein. Samples stored below room temperature but not frozen should be removed from refrigeration, gently rotated and allowed to come to room temperature before proceeding.

If the samples to be analyzed are whole blood specimens, the hematocrit (Hct) (also known as the packed cell volume or erythrocyte volume fraction) of each specimen will be required for ultimate determination of TPMT activity. If this information is not available for whole blood specimens to be analyzed, it should be determined before proceeding. If necessary, Hct may be determined by any method known in the art.

In preparation for incubation, samples containing RBC's (including whole blood specimens) may be further prepared by lysing the cells and release TPMT enzyme contained therein. Lysing the cells can be accomplished by any method known in the art, preferably by sufficiently lowering sample temperature to cause cell lysing. For example, the cells may be lysed by placing the samples in a freezer at a temperature of about −80° C. and held for a minimum of about 20 minutes.

A buffer may then be added to the frozen samples, and the mixture allowed to thaw to room temperature. In some embodiments, the buffer may be a phosphate buffer (preferably at a concentration of about 0.1 N).

Either 6-MP or SAM, preferably SAM, is then added to the room temperature samples. In preferred embodiments, an internal standard is also added to the samples at this time, and the resulting mixture gently vortexed to ensure homogeneity. As discussed above, in preferred embodiments, either the 6-MP or SAM is isotopically labeled, preferably SAM is isotopically labeled as $d_3$-SAM.

TPMT enzyme activity is affected by temperature, thus to accurately derive enzyme activity from a measured rate of metabolite formation, incubation should be conducted at a constant temperature. Preferably, the constant incubation temperature mimics normal body temperatures, i.e., about 37° C. Thus, prior to incubation, samples may be heated to about 37° C. and kept in an incubation heating block or water bath for the duration of the incubation period. To ensure that the temperature of the reaction mixture does not drop upon initiation of the incubation period, the final required reagent, preferably the 6-MP, should also be brought to the same temperature before being added to the incubation mixture.

Incubation is initiated when the final required reagent, preferably the 6-MP, is added to the reaction mixture. After a measured incubation period, the reaction may be quenched by rapidly reducing the temperature of the reaction mixture, for example by submersion in an ice bath. The preferred incubation period is about one hour.

In embodiments where neither reagent is isotopically labeled, the product of the TPMT catalyzed reaction between SAM and 6-MP is the enzyme product 6-MMP. In embodiments where an isotopically labeled reagent is used in the incubation mixture, the product of the TPMT catalyzed reaction between isotopically labeled SAM and 6-MP, or SAM and isotopically labeled 6-MP, is the enzyme product isotopically labeled 6-MMP. The concentration of 6-MMP in the analytical sample (or isotopically labeled 6-MMP, depending on reactants used) is related to enzyme activity. However, additional factors, such as sample dilution by addition of incubation reagents, Hct of the specimen, and non-enzyme catalyzed formation of 6-MMP (or isotopically labeled 6-MMP), should also be considered. Treatment of these factors is discussed in detail below. The incubated samples may now be prepared for mass spectrometric analysis.

Sample Preparation for Mass Spectrometric Analysis

In preparation for mass spectrometric analysis, 6-MMP and/or $d_3$-6-MMP may be enriched relative to other components in the sample (e.g. protein) by various methods known in the art, including for example, liquid chromatography, filtration, centrifugation, thin layer chromatography (TLC), electrophoresis including capillary electrophoresis, affinity separations including immunoaffinity separations, extraction methods including ethyl acetate or methanol extraction, and the use of chaotropic agents or any combination of the above or the like.

Protein precipitation is one method of preparing a test sample, especially a biological test sample, such as serum or plasma. Such protein purification methods are well known in the art, for example, Polson et al., *Journal of Chromatography B* 2003, 785:263-275, describes protein precipitation techniques suitable for use in methods of the present invention. Protein precipitation may be used to remove most of the protein from the sample leaving $d_3$-6-MMP in the supernatant. The samples may be centrifuged to separate the liquid supernatant from the precipitated proteins; alternatively the samples may be filtered to remove precipitated proteins. The resultant supernatant or filtrate may then be applied directly to mass spectrometry analysis; or alternatively to liquid chromatography and subsequent mass spectrometry analysis. In certain embodiments, the use of protein precipitation such as for example, formic acid protein precipitation, may obviate the need for TFLC or other on-line extraction prior to mass spectrometry or HPLC and mass spectrometry.

Another method of sample purification that may be used prior to mass spectrometry is liquid chromatography (LC). Certain methods of liquid chromatography, including HPLC, rely on relatively slow, laminar flow technology. Traditional HPLC analysis relies on column packing in which laminar flow of the sample through the column is the basis for separation of the analyte of interest from the sample. The skilled artisan will understand that separation in such columns is a diffusional process and may select LC, including HPLC, instruments and columns that are suitable for use with 6-MMP and/or $d_3$-6-MMP. The chromatographic column typically includes a medium (i.e., a packing material) to facilitate separation of chemical moieties (i.e., fractionation). The medium may include minute particles. The particles typically include a bonded surface that interacts with the various chemical moieties to facilitate separation of the chemical moieties. One suitable bonded surface is a hydrophobic bonded surface such as an alkyl bonded or a cyano bonded surface. Alkyl bonded surfaces may include C-4, C-8, C-12, or C-18 bonded alkyl groups. In preferred embodiments, the column is a C-18 column. The chromatographic column includes an inlet port for receiving a sample and an outlet port for discharging an effluent that includes the fractionated sample. The sample may be supplied to the inlet port directly or indirectly from a solid-phase extraction or TFLC column.

In one embodiment, the sample may be applied to the LC column at the inlet port, eluted with a solvent or solvent mixture, and discharged at the outlet port. Different solvent modes may be selected for eluting the analyte(s) of interest. For example, liquid chromatography may be performed using a gradient mode, an isocratic mode, or a polytyptic (i.e. mixed) mode. During chromatography, the separation of materials is effected by variables such as choice of eluent (also known as a "mobile phase"), elution mode, gradient conditions, temperature, etc.

In certain embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. Such procedures may enrich the amount of one or more analytes of interest relative to one or more other components of the sample.

In one preferred embodiment, HPLC is conducted with a polar embedded analytical column chromatographic system. In certain preferred embodiments, a polar embedded C-18 analytical column (e.g., a Synergi Fusion-RP analytical column from Phenomenex, Inc. (4 particle size, 100×3.0 mm), or equivalent) is used. In certain preferred embodiments, HPLC and/or TFLC are performed using HPLC Grade 0.1% aqueous formic acid and 100% acetonitrile as the mobile phases.

By careful selection of valves and connector plumbing, two or more chromatography columns may be connected as needed such that material is passed from one to the next without the need for any manual steps. In preferred embodiments, the selection of valves and plumbing is controlled by a computer pre-programmed to perform the necessary steps. Most preferably, the chromatography system is also connected in such an on-line fashion to the detector system, e.g., an MS system. Thus, an operator may place a tray of samples in an autosampler, and the remaining operations are performed under computer control, resulting in purification and analysis of all samples selected.

In some embodiments, TFLC may be used for purification of 6-MMP and/or $d_3$-6-MMP prior to mass spectrometry. In such embodiments, samples may be extracted using an TFLC extraction cartridge which captures the analyte, then eluted and chromatographed on a second TFLC column or onto an analytical HPLC column prior to ionization. For example, sample extraction with an TFLC extraction cartridge may be accomplished with a large particle size (50 μm) packed column. Sample eluted off of this column may then be transferred to an HPLC analytical column for further purification prior to mass spectrometry. In preferred embodiments, a polar embedded C-18 analytical column (e.g., a Cyclone P® column from Cohesive Technologies. Inc. (50 μm particle size, 1.0×50 mm), or equivalent) is used. Because the steps involved in these chromatography procedures may be linked in an automated fashion, the requirement for operator involvement during the purification of the analyte can be minimized. This feature may result in savings of time and costs, and eliminate the opportunity for operator error.

Detection and Quantitation by Mass Spectrometry

In various embodiments, 6-MMP and/or $d_3$-6-MMP present in a test sample may be ionized by any method known to the skilled artisan. Mass spectrometry is performed using a mass spectrometer, which includes an ion source for ionizing the fractionated sample and creating charged molecules for further analysis. For example ionization of the sample may be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), and particle beam ionization. The skilled artisan will understand that the choice of ionization method may be determined based on the analyte to be measured, type of sample, the type of detector, the choice of positive versus negative mode, etc.

6-MMP and/or $d_3$-6-MMP may be ionized in positive or negative mode. In preferred embodiments, 6-MMP and/or $d_3$-6-MMP is ionized by ESI in positive mode. In related preferred embodiments, 6-MMP and/or $d_3$-6-MMP ions are in a gaseous state and the inert collision gas is argon or nitrogen; preferably argon.

In mass spectrometry techniques generally, after the sample has been ionized, the positively or negatively charged ions thereby created may be analyzed to determine a mass-to-charge ratio. Suitable analyzers for determining mass-to-charge ratios include quadrupole analyzers, ion trap analyzers, and time-of-flight analyzers. Exemplary ion trap methods are described in Bartolucci, et al. *Rapid Commun. Mass Spectrum.* 2000, 14:967-73.

The ions may be detected using several detection modes. For example, selected ions may be detected, i.e. using a selective ion monitoring mode (SIM), or alternatively, when operating the instrument in MS/MS (tandem) mode, ions may be detected with, for example, multiple reaction monitoring (MRM). Preferably, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the RF signal, and the mass/charge ratio. The voltage and amplitude may be selected so that only ions having a particular mass/charge ratio travel the length of the quadrupole, while all other ions are deflected.

One may enhance the resolution of the MS technique by employing "tandem mass spectrometry," or "MS/MS". In this technique, a precursor ion (also called a parent ion) generated from a molecule of interest can be filtered in an MS instrument, and the precursor ion subsequently fragmented to yield one or more fragment ions (also called daughter ions or product ions) that are then analyzed in a second MS procedure. By careful selection of precursor ions, only ions produced by certain analytes are passed to the fragmentation chamber, where collisions with atoms of an inert gas produce the fragment ions. Because both the precursor and fragment ions are produced in a reproducible fashion under a given set of ionization/fragmentation conditions, the MS/MS technique may provide an extremely powerful analytical tool. For example, the combination of precursor ion selection/fragmentation may be used to eliminate interfering substances, and may be particularly useful in complex samples, such as biological samples.

The mass spectrometer typically provides the user with an ion scan; that is, the relative abundance of each ion with a particular mass/charge over a given range (e.g., 100 to 1000 amu) The results of an analyte assay, that is, a mass spectrum, may be related to the amount of the analyte in the original sample by numerous methods known in the art. For example, given that sampling and analysis parameters are carefully controlled, the relative abundance of a given ion may be compared to a table that converts that relative abundance to an absolute amount of the original molecule. Alternatively, molecular standards may be run with the samples, and a standard curve constructed based on ions generated from those standards. Using such a standard curve, the relative abundance of a given ion may be converted into an absolute amount of the original molecule. In certain preferred embodiments, an internal standard is used to generate a standard curve for calculating the quantity of 6-MMP and/or $d_3$-6-MMP. Methods of generating and using such standard curves are well known in the art and one of ordinary skill is capable of selecting an appropriate internal standard. For example, in preferred embodiments where the analyte of interest is isotopically labeled 6-MMP (e.g., $d_3$-6-MMP), non-isotopically labeled 6-MMP may be used as an internal standard; in other embodiments where the analyte of interest is 6-MMP, an isotopically labeled 6-MMP (e.g, $d_3$-6-MMP) may be used as an internal standard. Numerous other methods for relating the amount of an ion to the amount of the original molecule will be well known to those of ordinary skill in the art.

One or more steps of the methods may be performed using automated machines. In certain embodiments, one or more purification steps are performed on-line, and more preferably all of the purification and mass spectrometry steps may be performed in an on-line fashion.

In certain embodiments, such as MS/MS, where precursor ions are isolated for further fragmentation, collisionally activated dissociation (CAD), sometimes called collision-induced dissociation (CID), is often used to generate fragment ions for further detection. In CAD, precursor ions gain energy through collisions with an inert gas, and subsequently fragment. Sufficient energy must be deposited in the precursor ion so that certain bonds within the ion can be broken due to increased vibrational energy. See, e.g., Haddon, et al., *J. Am. Chem. Soc* 1968, 90:4745-46.

In particularly preferred embodiments, $d_3$-6-MMP in a sample is detected and/or quantified using MS/MS as follows. The samples are subjected to liquid chromatography, preferably TFLC followed by HPLC; the flow of liquid solvent from the chromatographic column enters the heated nebulizer interface of an MS/MS analyzer; and the solvent/analyte mixture is converted to vapor in the heated tubing of the interface. The analyte (e.g., $d_3$-6-MMP), contained in the nebulized solvent, is ionized by the corona discharge needle of the interface, which applies a large voltage to the nebulized solvent/analyte mixture. The ions, e.g. precursor ions, pass through the orifice of the instrument and enter the first quadrupole. Quadrupoles 1 and 3 (Q1 and Q3) are mass filters, allowing selection of ions (i.e., selection of "precursor" and "fragment" ions in Q1 and Q3, respectively) based on their mass to charge ratio (m/z). Quadrupole 2 (Q2) is the collision cell, where ions are fragmented. The first quadrupole of the mass spectrometer (Q1) selects for molecules with the mass to charge ratios of $d_3$-6-MMP. Precursor ions with the correct mass/charge ratios are allowed to pass into the collision chamber (Q2), while unwanted ions with any other mass/charge ratio collide with the sides of the quadrupole and are eliminated. Precursor ions entering Q2 collide with neutral argon gas molecules and fragment. The fragment ions generated are passed into quadrupole 3 (Q3), where the fragment ions of $d_3$-6-MMP are selected while other ions are eliminated.

The methods may involve MS/MS performed in either positive or negative ion mode; preferably positive ion mode. Using standard methods well known in the art, one of ordinary skill is capable of identifying one or more fragment ions of a particular precursor ion of $d_3$-6-MMP that may be used for selection in quadrupole 3 (Q3).

As ions collide with the detector they produce a pulse of electrons that are converted to a digital signal. The acquired data is relayed to a computer, which plots counts of the ions collected versus time. The resulting mass chromatograms are similar to chromatograms generated in traditional HPLC-MS methods. The areas under the peaks corresponding to particular ions, or the amplitude of such peaks, may be measured and correlated to the amount of the analyte of interest. In certain embodiments, the area under the curves, or amplitude of the peaks, for fragment ion(s) and/or precursor ions are measured to determine the amount of 6-MMP and/or isotopically labeled 6-MMP. As described above, the relative abundance of a given ion may be converted into an absolute amount of the original analyte using calibration standard curves based on peaks of one or more ions of an internal molecular standard.

Although $d_3$-SAM is used as the isotopically labeled reactant in the Examples below, it is contemplated that other isotopically labeled reactants may be similarly used in the methods of the present invention. For example, d-SAM or $d_2$-SAM may be used as an isotopically labeled reactant by selecting the appropriate parent ion mass to charge ratio (i.e., 168.1 for d-6-MMP and 169.1 for $d_2$-6-MMP) for fragmentation and generation of fragments of mass to charge ratio of 125.1.

Calculation of TPMT Enzyme Activity

Enzyme activity, a measure of enzyme concentration, is most often given in terms of enzyme units (EU), where an EU is the amount of enzyme product produced in one hour under standard conditions in units of nmole/hr/mL RBC. Expressed in this way, the EU calculation is normalized to 1.0 mL RBC and 1 hour incubation, in accordance with units typically reported in the art. In embodiments where the sample is a whole blood specimen, the hematocrit of the whole blood specimen is used to convert whole blood volume to RBC volume.

Thus for a whole blood sample, EU is calculated according to equation (1):

$$\text{TPMT EU} = K^*[\text{enzyme product}]/Hct \quad (1)$$

where:
EU=Enzyme units in nmole/hr/mL RBC at 37° C.;
K=Conversion constant
[enzyme product]=measured concentration of $d_3$-6-MMP or 6-MMP; and
Hct=hematocrit value for whole blood sample.

The conversion constant, K, is used to convert concentration values of the enzyme product (ng/mL) in the sample analyzed by mass spectrometry to nmoles/mL in the original sample. The conversion constant is calculated by dividing the dilution factor (DF) of the sample analyzed by mass spectrometry by the molecular weight of the enzyme product. For example, in embodiments where the detected enzyme product is $d_3$-6-MMP, the conversion constant=DF/170.1; but in embodiments where the detected enzyme product is 6-MMP, the conversion constant=DF/167.1.

As used herein, the term dilution factor indicates a multiplicative factor that accounts for addition of various reagents and solutions, such as incubation reagents, buffer solution, and internal standards, to the original sample through the course of incubation and preparation for mass spectroscopic analysis. Exemplary calculations for determining the dilution factor are demonstrated below in Example 5.

The following Examples serve to illustrate the invention. These Examples are in no way intended to limit the scope of the methods. In particular, the following Examples demonstrate formation of $d_3$-6-MMP as the enzyme product, quantitation of $d_3$-6-MMP by mass spectrometry, and the use of 6-MMP as an internal standard. The use of 6-MMP as an internal standard is not meant to limiting in any way, Any appropriate chemical species, easily determined by one in the art, may be used as an internal standard for either $d_3$-6-MMP or 6-MMP quantitation.

EXAMPLES

Example 1

Reagent Preparation

Two calibrant solutions were prepared with $d_3$-6-MMP (Medical Isotopes, Inc., Cat. No. D3280, or equivalent). A $d_3$-6-MMP calibrant stock solution of about 800 ng/μL $d_3$-6-MMP in 0.1 N NaOH solution was prepared. A 15.0 μL portion of the $d_3$-6-MMP calibrant stock solution was then diluted with about 5.00 mL 0.1% Formic acid solution to prepare a $d_3$-6-MMP calibrant working solution of about 2.39 ng/μL.

Two internal standard solutions were prepared with 6-MMP (MP Biomedicals, Cat. No. 102332, or equivalent). A 6-MMP internal standard stock solution of about 1000 ng/mL 6-MMP in 0.1 N NaOH was prepared. A 16.0 μL portion of the 6-MMP internal standard stock solution was then diluted with about 8.00 mL of 0.1% Formic acid solution to prepare a 6-MMP internal standard working solution of about 2.00 ng/μL.

A $d_3$-SAM incubation solution was prepared with $d_3$-SAM (C/D/N Isotopes, Cat. No. D-4093, or equivalent) in 0.1 N phosphate buffer solution at a concentration of about 860 μM $d_3$-SAM.

A 6-MP incubation solution was prepared with 6-MP (Sigma Aldrich, Cat. No. 63810-5G-F, or equivalent) in 0.1 N NaOH solution at a concentration of about 58.75 μM 6-MP.

Example 2

Quality Control and Patient Sample Preparation and Incubation

Patient samples consisting of whole blood specimens of about 3-5 mL were collected in Vacutainer tubes with EDTA. Patient samples were stored at 4° C., and immediately prior to analysis, allowed to come to room temperature while being gently rotated.

150 μL of each whole blood specimen was transferred to a polypropylene sample tube. The hematocrit of each whole blood specimen was determined from the remainder of the specimen and recorded.

The sample tubes were placed in an −80° C. freezer for a minimum of 20 minutes in order to lyse RBC's and release TPMT in the samples. Upon removal from the freezer, 450 μL of 0.1 N phosphate buffer solution were added to each tube. The mixtures were allowed to thaw to room temperature and gently vortexed at low speed until thoroughly mixed.

In preparation for incubation, 200 μL of each sample were transferred to a glass culture, mixed with 400 μL of 0.1 N phosphate buffer, 35 μL of $d_3$-6-SAM incubation solution, 35 μL of 6-MMP internal standard working solution, and preheated to 37° C. At a precise time, 40 μL of 6-MP incubation solution (also preheated to 37° C.) were added to each sample and gently agitated to mix. The resulting mixtures were incubated for 60 minutes at 37° C.

After 60 minutes of incubation, the enzyme reactions were quenched by moving, the samples into an ice bath. The samples were kept in the ice bath until transferred to a 96-well plate.

Quality control (QC) samples were prepared similarly to the patient samples above. About 8 mL of whole blood were obtained in two EDTA Vacutainer tubes from a reference volunteer donor. The contents of the two tubes were pooled and two Hct measurements taken. Three QC samples (QC-H, QC-M, and QC-L) were prepared by first transferring 150 μL of the pooled whole blood to polypropylene sample tubes. The QC samples were frozen and thawed with the addition of 450 μL of 0.1 N phosphate buffer solution, as above.

Incubation mixtures for QC-H, QC-M, and QC-L were prepared from 200 μL, 100 μL, and 50 μL of the QC sample, respectively, and enough phosphate buffer to bring the total for each to 600 μL. 35 μL, of $d_3$-6-SAM incubation solution and 35 μL of 6-MMP internal standard working solution were added and the mixture preheated to 37° C. The QC samples were then incubated according to the procedure described above.

Example 3

Extraction of $d_3$-6-MMP from Samples using Liquid Chromatography

200 μL each of a reagent blank, the incubated quality control samples, and the incubated patient samples were then transferred to a 96-well plate. Sample injection was performed with a Cohesive Technologies Aria TX-2 HTLC system using Aria OS V 1.5.1 or newer software.

The HTLC system automatically injected 30 μL of the above prepared samples into a Cyclone P® column (50×1.0 mm, 50 μm polar embedded C-18 column from Cohesive Technologies) packed with large particles. The samples were loaded at a high flow rate (5.0 mL/min, loading reagent 0.1% formic acid) to create turbulence inside the extraction column. This turbulence ensured optimized binding of $d_3$-6-MMP and 6-MMP to the large particles in the column and the passage of residual protein and debris to waste.

Following loading, the flow direction was reversed and the sample eluted off to the analytical column (polar embedded C-18 Synergi Fusion-RP, 4 μm particle size, 100×3 mm). A binary HPLC gradient was applied to the analytical column, to separate $d_3$-6-MMP and 6-MMP from other analytes contained in the sample. Mobile phase A was 0.1% formic acid and mobile phase B was 100% acetonitrile. The HPLC gradient started with a 5% organic gradient which was stepped to 20% in approximately 105 seconds, then stepped to 40% in approximately 235 seconds. The separated sample was then subjected to MS/MS for quantitation of $d_3$-6-MMP and 6-MMP.

Example 3

Detection and Quantitation of $d_3$-6-MMP by MS/MS

MS/MS was performed using an Applied Biosystems API 2000 MS/MS system. The following software programs were used in the Examples described herein: Analyst Mass Spectrometer Instrument Control and Data Processing System, v.1.4.1, Build 1200, 2004 (Applied Biosciences, Foster, Calif.). Liquid solvent/analyte exiting the analytical column flowed to the heated nebulizer interface of an Applied Biosystems API 2000 MS/MS analyzer. The solvent/analyte mixture was converted to vapor in the heated tubing of the interface. Analytes in the nebulized solvent were ionized by positive ion ESI.

Ions passed to the first quadrupole (Q1), which selected ions with a mass to charge ratio of 170.1±0.50 m/z. Ions entering Quadrupole 2 (Q2) collided with argon gas to generate ion fragments, which were passed to quadrupole 3 (Q3) for further selection. Simultaneously, the same process using isotope dilution mass spectrometry was carried out with an internal standard, 6-MMP. The following mass transitions were used for detection and quantitation during validation on positive polarity.

TABLE 1

Mass Transitions for $d_3$-6-MMP and 6-MMP (Positive Polarity)

| Analyte | Precursor Ion (m/z) | Product Ion (m/z) |
|---|---|---|
| $d_3$-6-MMP | 170.10 | 125.1 |
| 6-MMP | 167.10 | 125.1 |

Example 4

Intra-assay and Inter-assay Precision and Accuracy

Three quality control (QC) pools were prepared from lysed whole blood specimens spiked with $d_3$-6-MMP to a concentration of about 13, 42, and 98 ng/mL.

Six aliquots from each of the three QC pools were analyzed in a single assay to determine the coefficient of variation (CV (%)) of a sample within an assay. Results are found in Table 2. All accuracies are within an acceptable range of 85% to 115%.

TABLE 2

Intra-Assay Variation and Accuracy for $d_3$-6-MMP

| Sample | Level I (13.2 ng/mL) | Level II (42.8 ng/mL) | Level III (98.7 ng/mL) |
|---|---|---|---|
| 1 | 11.9 | 40.2 | 89.5 |
| 2 | 9.8 | * | 88.7 |
| 3 | 12.2 | 39.4 | 83.1 |
| 4 | 11.8 | 39.0 | 94.5 |
| 5 | 11.3 | 40.2 | 87.7 |
| 6 | 12.3 | 36.4 | 89.9 |
| Mean (ng/mL) | 11.5 | 39.0 | 88.9 |
| Standard Deviation (ng/mL) | 0.94 | 1.56 | 3.68 |
| CV (%) | 8.2% | 4.0% | 4.1% |
| Accuracy (%) | 87% | 91% | 90% |

Three aliquots of each of the same three QC pools were assayed over five days to determine the coefficient of variation (CV (%)) between assays. Results are found in Table 3. All accuracies are within an acceptable range of 85% to 115%.

TABLE 3

Inter-Assay Variation and Accuracy

| Mean for Each Day | Level I (13.2 ng/mL) | Level II (42.8 ng/mL) | Level III (98.7 ng/mL) |
|---|---|---|---|
| 1 | 11.57 | 38.05 | 88.4 |
| 2 | 12.07 | 37.82 | 92.4 |
| 3 | 15.42 | 49.82 | 123.67 |
| 4 | 12.73 | 49.03 | 119.33 |
| 5 | 13.12 | 42.90 | 100.73 |
| Mean (ng/mL) | 13.0 | 43.5 | 104.9 |
| Standard Deviation (ng/mL) | 0.9 | 1.6 | 3.9 |
| CV (%) | 6.7% | 3.7% | 3.7% |
| Accuracy (%) | 98.7% | 101.8% | 106.3% |

Example 5

Calculation of TPMT Enzyme Unit (EU) Values from Enzyme Product Concentration

The enzyme activity, a measure of enzyme concentration, is given in terms of the amount of $d_3$-6-MMP (enzyme product) produced in one hour under standard conditions in units of nmole/hr/mL RBC. The EU calculation is normalized to 1.0 mL of RBC and a 1 hour incubation in accordance with units typically reported in the art. Because these Examples were conducted with whole blood specimens, the hematocrit is used to convert the whole blood volume to volume of RBC.

As discussed above, EU is calculated according to equation (1) for a whole blood sample:

$$\text{TPMT EU} = K*[\text{enzyme product}]/Hct \quad (1)$$

where:
 EU=Enzyme units in nmole/hr/mL RBC at 37° C.;
 K=Conversion constant
 [enzyme product]=measured concentration of $d_3$-6-MMP or 6-MMP; and
 Hct=hematocrit value for whole blood sample.

Enzyme product concentration, [enzyme product], is measured by the assay of the present invention, and the hematocrit, Hct, is measured for each whole blood specimen analyzed. The conversion constant, K, is calculated by determining the dilution factor resulting from the addition of phosphate buffer during specimen preparation steps, as well as the addition of incubation reagents to the incubation mixture. For example, as described in Examples 1 and 2, 450 µL of phosphate buffer is added to 150 µL of a lysed whole blood specimen prior to preparation of the incubation mixture, giving a first dilution factor of 4 to 1. 200 µL of this diluted lysed sample is then combined with 600 µL of phosphate buffer, 35 µL of $d_3$-SAM, 35 µL of internal standard solution, and 40 µL of 6-MP, giving a second dilution factor of 3.55 to 1. The cumulative dilution factor is the first dilution factor times the second dilution factor, or 14.2.

TABLE 4

Dilution Factor for Exemplary Sample Preparation and Incubation

| Action | Volume, µL | Factor |
|---|---|---|
| Sample Preparation: | | |
| Sampled volume of whole blood | 150 | |
| Phosphate buffer added to lysate | 450 | |
| Total diluted lysate volume: | 600 | 4.00 |
| Incubation: | | |
| Diluted lysate solution | 200 | |
| Phosphate buffer | 400 | |
| $d_3$-SAM | 35 | |
| Internal standard | 35 | |
| 6-MP | 40 | |
| Total Incubate Vol: | 710 | 3.55 |
| Cumulative Dilution Factor, DF: | | 14.20 |

Example 6

Analytical Sensitivity: Limit of Detection (LOD) and Lower Limit of Quantitation (LLOQ)

Figure 1:
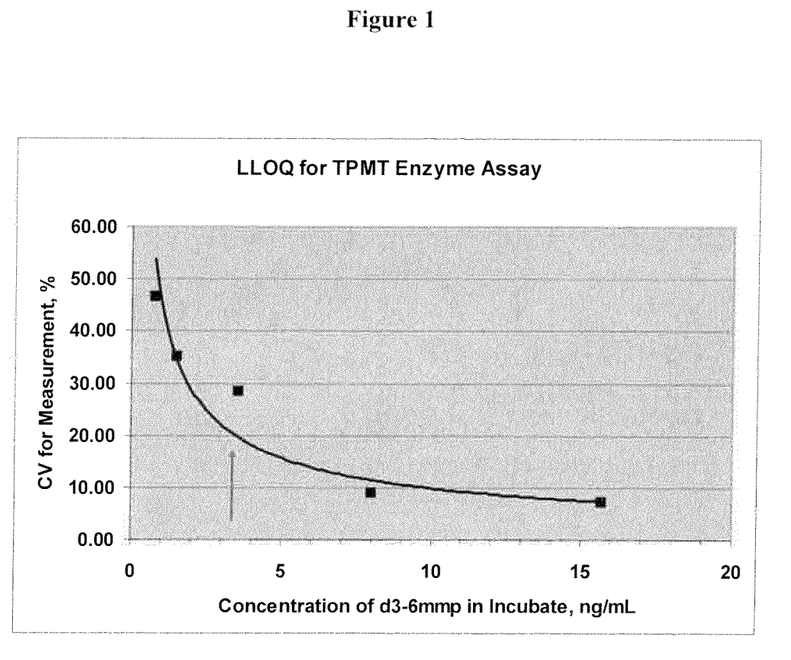
FIG. 1 shows a plot of the coefficient of variation of assays of five standards used to determine the limit of quantitation of the $d_3$-6-MMP assay. Details are discussed in Example 6.

The LLOQ is the point where measurements become quantitatively meaningful. The analyte response at the LLOQ is identifiable, discrete and reproducible with a precision of greater than 20%. The LLOQ was determined by assaying whole blood specimens from a homozygous individual with presumptive zero TPMT spiked with $d_3$-6-MMP concentrations of 0.82, 2.06, 4.11, 9.87, and 20.56 ng/mL (four replicates at each level) then determining the CV. The results were plotted (shown in FIG. 1) and the LLOQ was determined from the curve to be 3.2 ng/mL. The corresponding activity of TPMT is approximately 1.31 TPMT Enzyme Units (nmole $d_3$-6-MMP/hour/ml, RBC) for a specimen with a hematocrit of 0.4. Unspiked specimens were used as a blank to correct for any residual TPMT activity and for non-enzymatic reaction of the substrates.

The LOD is the point at which a value is beyond the uncertainty associated with its measurement and is defined as three standard deviations from the zero concentration. To determine the LOD for the $d_3$-6-MMP assay, samples of whole blood specimens incubated without 6-MP were run in seven replicates. The results of these assays were statistically analyzed with a mean value of 2.93 ng/mL, and a standard deviation of 0.44 ng/mL. Thus, the LOD for the $d_3$-6-MMP was 1.32 ng/mL, corresponding to 0.55 TPMT Enzyme units for a specimen with a hematocrit of 0.4.

Example 7

$d_3$-6-MMP Reportable Range and Linearity

Figure 2:
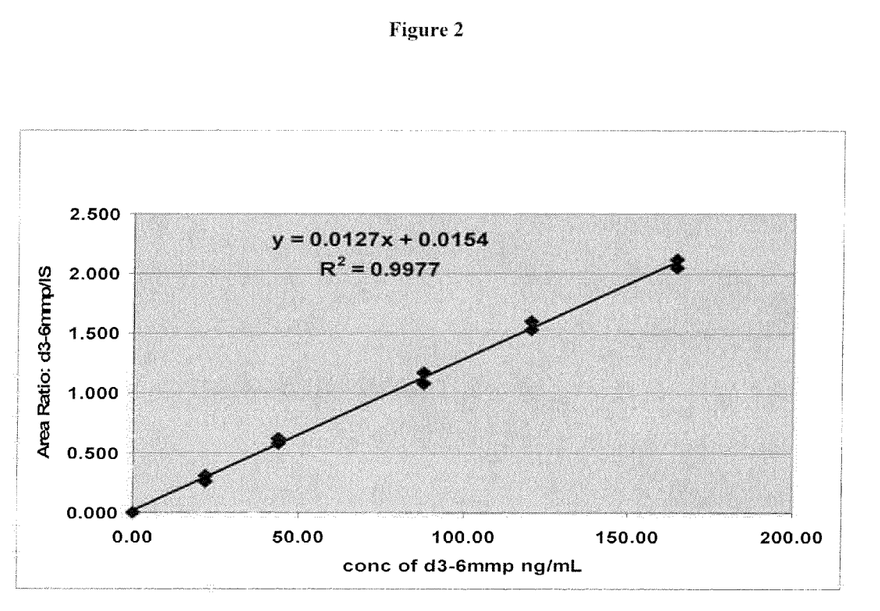
FIG. 2 shows the linearity of the quantitation of $d_3$-6-MMP in serially diluted stock samples using an LC-MS/MS assay. Details are described in Example 7.

To establish the linearity of $d_3$-6-MMP detection in the assay, one blank assigned as zero standard and five spiked dilute incubation mixtures consisting of 200 µL of lysed whole blood, the requisite amounts of $d_3$-SAM substrate, internal standard, and 0.1 N phosphate buffer incubated for one hour were prepared and analyzed multiple times over a 6 month period. The 6-MP substrate was excluded from the samples in order to prevent formation of $d_3$-6-MMP by endogenous TPMT. Using a linear calibration model without weighting, linear response in peak area ratios between analyte ($d_3$-6-MMP) and internal standard was obtained from zero to approximately 180 ng/mL $d_3$-6-MMP. The upper calibration limit corresponds to about 3 times the average enzyme units of TPMT for specimens of average hematocrit of about 0.4. Specimens of both higher hematocrit and high TPMT may yield concentrations of approximately 2.5 times the population mean value of about 60 ng/mL, i.e., 150 ng/mL in the diluted incubate, based on published reference range data by Ford, et al., *Ann. Clin. Biochem.* 2006, 43:354-60 for whole blood measurements of TPMT. Representative calibration data are shown in FIG. 2. Linear regression gave an average correlation coefficient ($R^2$) of 0.9970 over twelve calibrations.

Based on the calibration and LLOQ data, the quantifiable range of the TPMT assay is 1.3 to 60 TPMT Enzyme Units for specimens with a hematocrit of 0.4. The upper limit of 60 TPMT Enzyme Units is more than twice the highest TPMT level ever reported in human whole blood specimens. If the hematocrit of a specimen is 0.2, the quantifiable range is 2.6 to 120 TPMT Enzyme Units, by extrapolation.

Example 8

Recovery Studies

Pooled quality control (QC) samples were spiked with three levels of $d_3$-6-MMP (low QC, mid QC and high QC), and incubation carried out through the standard 1 hour at 37° C., with the absence of 6-MP, The low, mid, and high QC samples had concentrations of 13.2, 42.8, and 98.7 ng/mL, respectively.

A recovery study of these $d_3$-6-MMP spiked samples was performed (six assays at each concentration). Absolute recovery was calculated by dividing the $d_3$-6-MMP concentration detected in the pooled samples by the expected $d_3$-6-MMP concentration in samples. The mean recoveries were 87.72%, 91.28%, and 90.07%, respectively. All recoveries were acceptable, i.e., within the range of 80% to 120%.

Example 9

Specimen Stability Studies

Specimen stability studies were conducted by storing whole blood specimens in either EDTA or Heparin Vacutainer® tubes. Whole blood specimens were spiked with $d_3$-6-MMP and stored for 2, 15, and 27 days. The specimens were analyzed as outlined above, with results presented in Table 9. Note that the results shown in Table 9 have not been corrected for a reagent blank. The data is presented here merely to demonstrate the effect of time on stored samples. The data indicate that samples stored at 4° C. are likely to remain viable for at least 15 days.

TABLE 5

Standard stability for specimens stored for 2, 15, and 27 days in EDTA or Heparin sample tubes.

| Day | Patient 1 | | | Patient 2 | | |
|---|---|---|---|---|---|---|
| | EDTA Tube | Heparin Tube | Mean | EDTA Tube | Heparin Tube | Mean |
| 2 | 22.1 | 20.7 | 21.4 | 20.3 | 18.3 | 19.3 |
| 15 | 24.1 | 18.2 | 21.2 | 19.2 | 18.9 | 19.1 |
| 27 | 18.0 | 14.4 | 16.2 | 15.9 | 14.1 | 15.0 |

The contents of the articles, patents, and patent applications, and all other documents and electronically available information mentioned or cited herein, are hereby incorporated by reference in their entirety to the same extent as if each individual publication was specifically and individually indicated to be incorporated by reference, Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," "containing". etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

That which is claimed is:

1. A method for determining thiopurine-S-methyl transferase (TPMT) activity in a patient prior to initiation of 6-MP administration, said method comprising:
   a. incubating a sample obtained from a patient for a specified period of time with an isotopically labeled substrate for TPMT under conditions suitable for the generation of an isotopically labeled 6-methylmercaptopurine (6-MMP) product by TPMT in the sample, thereby forming an incubated sample;
   b. ionizing said isotopically labeled 6-methylinercaptopurine (6-MMP) from said incubated sample under conditions suitable to produce one or more ions detectable by mass spectrometry;
   c. determining the amount of one or more ions by mass spectrometry;
   d. using the amount of said one or more ions to determine the amount of isotopically labeled 6-methylmercaptopurine (6-MMP) in said incubated sample; and
   e. using the amount of isotopically labeled 6-MMP determined in said incubated sample to determine TPMT activity in the patient.

2. The method of claim 1, wherein said incubating comprises incubating said sample in the presence of isotopically labeled S-adenosylmethionine (SAM).

3. The method of claim 2, wherein said isotopically labeled S-adenosylmethionine (SAM) is $d_3$-S-adenosylmethionine ($d_3$-SAM).

4. The method of claim 3, wherein said isotopically labeled 6-MMP is $d_3$-6-methylmercaptopurine ($d_3$-6-MMP).

5. The method of claim 1, wherein said mass spectrometry is tandem mass spectrometry.

6. The method of claim 5, wherein said one or more ions detectable by mass spectrometry are selected from the group of ions consisting of ions with mass to charge ratios of 170.1±0.5., 152.1±0.5, 137.1±0.5, 136.1±0.5, 126.1±0.5., 125.1±0.5, 119.1±0.5, 99.1±0.5. 98.1±0.5, and 92.1±0.5.

7. The method of claim 5, wherein said one or more ions detectable by mass spectrometry comprise a precursor ion with a mass to charge ratio of 170.1±0.5, and a fragment ion with a mass to charge ratio of 125.1±0.5.

8. The method of claim 1, wherein said isotopically labeled 6-MMP in said incubated sample has been purified with liquid chromatography (LC) prior to ionization.

9. The method of claim 8, wherein said LC comprises high performance liquid chromatography (HPLC).

10. The method of claim 1, wherein said isotopically labeled 6-MMP in said incubated sample has been purified with solid phase extraction (SPE) prior to ionization.

11. The method of claim 10, wherein said SPE comprises turbulent flow liquid chromatography (TFLC).

12. The method of claim 1, wherein a normal TPMT activity in the patient indicates that initiation of treatment with 6-MP is safe for the patient.

13. The method of claim 1, wherein a TPMT activity in the patient of less than normal TPMT activity but greater than nominally zero TPMT activity indicates that treatment of the patient with 6-MP should be initiated at a reduced dosage relative to normal.

14. The method of claim 1, wherein a TPMT activity in the patient of nominally zero TPMT activity indicates that treatment of the patient with 6-MP should not be initiated.

* * * * *

UNITED STATES PATENT AND TRADEMARK OFFICE
CERTIFICATE OF CORRECTION

PATENT NO. : 8,497,471 B2  
APPLICATION NO. : 13/232861  
DATED : July 30, 2013  
INVENTOR(S) : William F. Haddon and Nigel J. Clarke Page 1 of 1

It is certified that error appears in the above-identified patent and that said Letters Patent is hereby corrected as shown below:

IN THE CLAIMS

Claim 1, Column 26, line 17
Delete "6-methylinercaptopurine" and insert --6-methylmercaptopurine--.

Signed and Sealed this
Twenty-ninth Day of October, 2013

Teresa Stanek Rea
*Deputy Director of the United States Patent and Trademark Office*